(12) United States Patent
Del Giglio

(10) Patent No.: US 6,416,493 B1
(45) Date of Patent: *Jul. 9, 2002

(54) METHOD AND SYSTEM FOR THE TREATMENT OF HYPERKINETIC ATRIAL ARRHYTHMIA

(76) Inventor: Mauro Del Giglio, Villaggio Santa Barbara 394, I-52022 Cavriglia (Arezzo) (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/884,567

(22) Filed: Jun. 27, 1997

(30) Foreign Application Priority Data

Jun. 27, 1996 (IT) .......................... FI96A0154

(51) Int. Cl.[7] .............................. A61M 29/00
(52) U.S. Cl. ................. 604/96.01; 604/20; 604/67; 604/97.01; 604/99.04; 604/101.05; 604/247; 600/381
(58) Field of Search .............. 604/19, 20, 65, 604/66, 67, 96, 247, 246, 96.01, 97.01, 98.01, 99.01, 99.02, 99.03, 99.04, 101.01, 101.03, 101.05; 600/18, 377, 381

(56) References Cited

U.S. PATENT DOCUMENTS

| 3,981,299 | A | | 9/1976 | Murray |
| 4,146,029 | A | | 3/1979 | Ellinwood, Jr. |
| 4,723,946 | A | | 2/1988 | Kay |
| 4,973,319 | A | | 11/1990 | Melsky |
| 5,286,254 | A | * | 2/1994 | Shapland et al. ............. 604/96 |
| 5,569,198 | A | * | 10/1996 | Racchini ...................... 604/20 |
| 5,730,137 | A | * | 3/1998 | Amano et al. .............. 604/662 |

FOREIGN PATENT DOCUMENTS

| EP | 0 335 205 | | 10/1989 |
| EP | 0 429 141 | | 5/1991 |
| EP | 0429141 | * | 5/1991 |

\* cited by examiner

*Primary Examiner*—Ronald Stright
(74) *Attorney, Agent, or Firm*—Popovich & Wiles, PA

(57) ABSTRACT

A method and device for the pharmacological cardioversion of fibrillation or atrial flutter is disclosed. The device is implantable in the human body and provides equipment for drug infusion using an electrocatheter positioned in the right atrium, the right ventricle, or the coronary sinus. The electrocatheter is provided with sensors which monitor the electromechanical activity of the heart and which intervene to activate the infusion in the presence of fibrillation or flutter. The catheter may be provided with at least one balloon which can be inflated and deflated to create a chamber which permits perfusion of the drug directly into the vein of Marshall.

10 Claims, 7 Drawing Sheets

METHOD AND SYSTEM FOR THE TREATMENT OF HYPERKINETIC ATRIAL ARRHYTHMIA

FIELD OF THE INVENTION

This invention is in the field of implantable medical devices. More particularly, the invention is in the field of implantable devices for the detection and interruption of hyperkinetic atrial arrhythmia.

BACKGROUND

Hyperkinetic atrial arrhythmia includes a large number of generally benign disorders characterised by an increase in the frequency of atrial contraction, possibly accompanied by an increase in frequency of ventricular contraction. These increases can lead to fibrillation and flutter in which the movement of the atrium is chaotic and does not correspond to that of the ventricle.

Clinical electrocardiograms may suggest the following risks for the patient: atrial tachycardia (from 140 to 220 bpm) caused by heart disease which can result in a net reduction in the cardiac output due to reduced atrial and ventricular filling in combination with hypotension and lipothymia; atrio-ventricular junctional tachycardia with feedback of the P wave and a reduction in cardiac output; multiform supraventricular tachycardia from different atrial pacemakers functioning separately, with extreme variability of cardiac frequency; atrial flutter, in which the frequency of atrial contraction is more than 200 bpm, with a variable ventricular response depending on the conduction ratio (2:1, 3:1 etc.); and atrial fibrillation, comprising a chaotic movement of the atria which become distended and do not empty properly.

Among these atrial tachyarrhythmias, flutter and fibrillation are without doubt the most disabling. In particular, atrial fibrillation (hereafter "AF") is an arrhythmia which can cause numerous problems.

For example, from the haemodynamic point of view, AF results in an absence of atrial systole which, in a normally functioning heart, increases ventricular filling by increasing both the velocity and the volume of blood flow. Its absence therefore reduces cardiac output. AF also leads to a pooling of the blood in the atrium, which favors the formation of thromboembolism. This condition is life-threatening to the patient. The irregularity of the ventricular response to the chaotic electrical activity in AF may also lead to unrestrained ventricular tachyarrhythmia, which is even more dangerous than atrial tachyarrhythmia.

The treatment of AF (and in certain cases, of atrial flutter also) consists of correcting the sinus rhythm by cardioversion. Cardioversion may be achieved using pharmacological or electrical intervention. In the latter case, a suitable anticoagulation procedure is necessary in combination with an anaesthetic or sedation being administered prior to administration of the electric shock. Pharmacological cardioversion also requires anticoagulation, but not anaesthesia, and gives rise to a longer therapeutic effect. Anticoagulation usually is not necessary if cardioversion is performed in the first 48 hours after the onset of arrhythmia.

Despite the foregoing, a need exists for a method and apparatus capable of detecting AF at its onset and interrupting it before it reaches an advanced stage.

SUMMARY OF THE INVENTION

The invention relates to an implantable device adapted for the detection and interruption of hyperkinetic atrial arrhythmia. More particularly, the invention relates to a device comprising a catheter positioned in the heart which is connected to a system for detecting AF and intervening during the early stages of AF using a drug, electrical stimulation or both. The catheter includes a first lumen capable of perfusing a drug, and optionally at least one additional lumen for inflating and deflating one or more optional balloons which, during the infusion, isolate portions of the vascularture, thereby creating conditions which allow the drug to reach the coronary arteries and the vein of Marshall. The catheter is operably connected to a housing which includes a reservoir for the drug, a system for inflating and deflating the vessel closure balloons, if they are provided, a system for infusing a bolus of drug, a sensing system for detecting atrial fibrillation in electrical or electromechanical communication with sensors, a system for the electrostimulation of the heart in arrhythmic emergencies, a two-way telemetry system for setting the infusion, sensing, and simulation parameters, and a valve port for filling the necessary drug reservoir from outside the body. The system may also include external telemetric instrumentation for programming the implanted device.

DETAILED DESCRIPTION

In the past, cardioversion of AF by means of intravenous drug infusion has been applied to patients in which the problem is of recent origin, or to patients that have been subjected to treatment with anticoagulant drugs.

Since it is not always possible to be immediately aware of the onset of AF and, therefore, to intervene using normal procedures, the present invention provides a method for pharmacological atrial cardioversion by means of a device which can be implanted like a normal cardiac pacemaker. Upon onset of AF (detected by an electrical, electromechanical or similar sensor) the quantity and the type of drug necessary to obtain cardioversion of the atrium is injected into the coronary sinus (CS), at the edge of the right atrium (RA), or the right ventricle (RV).

Figure 1:
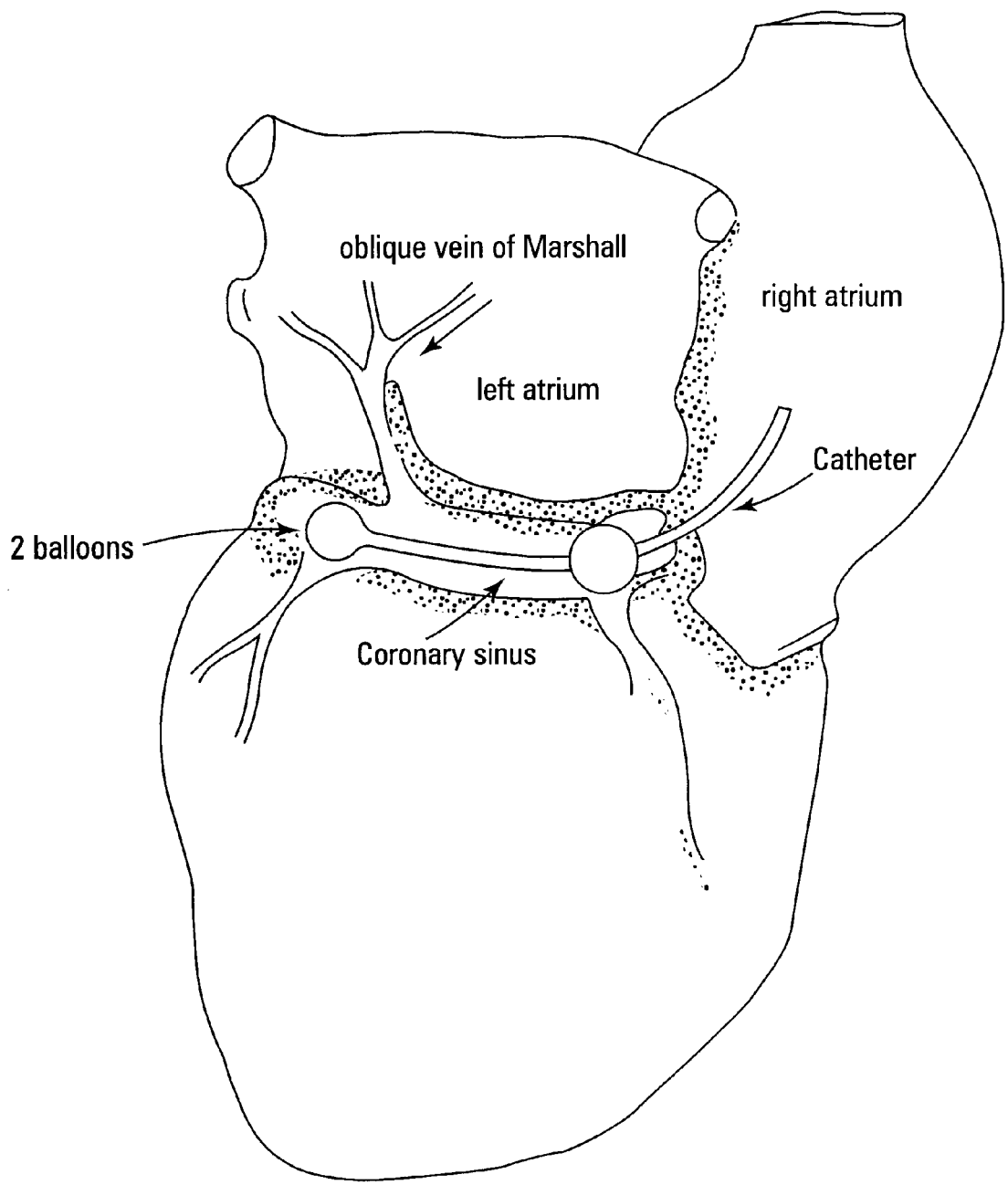
FIG. 1 is a schematic depiction of the heart seen from the rear with a catheter having two inflated balloons occluding a portion of the coronary sinus.

Infusion of the drug through the CS has been found to significantly reduce the quantity of drug necessary for defibrillation, thus also reducing the possibility of secondary effects which can arise as the result of heavy drug use, as is necessary with the intravenous approach, and even in atrial or ventricular infusion. In fact, CS infusion with the system described below enables direct coronary diffusion from the CS, by virtue of the presence of the vein of Marshall which carries blood directly from the atrial wall into the CS itself (FIG. 1) and which can therefore transport the infused drug backwards in the CS.

The implantable system of the present invention includes a catheter insertable through the venous system passing, for example, from the superior vena cava to the CS. The catheter includes a first lumen capable of perfusing a drug, and an optional additional lumen for inflating and deflating one or more optional balloons which, during the infusion, create the conditions for the drug to reach the coronary arteries and the vein of Marshall. The possible configurations of the distal part of the catheter to be located in the CS are described below.

Where the drug is delivered to the atrium or ventricle, the catheter needs only one lumen for the infusion of the drug. The outlet hole of the lumen opens into the atrium or ventricle and is protected by a non-return valve or similar system.

In addition to the lumens necessary for the hydraulic functions, (i.e., balloon inflation), the catheter includes one or more conductors which are connected to electrodes and/or sensors. The electrodes detect the onset of AF and, alternatively or contemporaneously, stimulate the heart or the atrium during arrhythmic situations.

The implantable system further includes a housing made from a biocompatible material and having an inert seal. The electrocatheter described above is connected to the housing. The housing contains: a) a reservoir for the drug; b) a system for inflating and deflating the vessel closure balloon or balloons, if such balloons are to be used; c) a system for the infusion of a bolus of drug in a programmable quantity; d) a sensing system for detecting AF (and therefore cardiac activity), connected to electrical or electromechanical sensors; e) a system for the electrical stimulation of the heart in arrhythmic emergencies; f) a two-way telemetry system for setting the infusion, sensing and stimulation parameters; and g) a valve port for filling the drug reservoir from outside the body.

The system may also employ external telemetric instrumentation for programming the implanted device, which is operatively similar to that used in existing cardiac pacemakers.

The system operates as follows. The AF sensor, preferably located in the CS or the atrium, detects the onset of AF and, after a short interval, initiates treatment in the following sequence: a) the balloon or balloons, if present, are inflated and inserted in the CS; b) a suitable pump injects the drug at the programmed pressure and quantity; and c) after a short interval (several seconds) the balloon(s) are deflated, thereby reestablishing the passage through the CS.

The treatment described above may be carried out, according to necessity and the opinion of the cardiologist, by means of a single bolus of drug which perfuses the tissue at a therapeutic quantity or, alternatively, with a timed series of reduced infusions so as to achieve the therapeutic quantity, building up the effect of the drug.

The use of a timed series of reduced infusions appears to be better tolerated and is therefore believed to be less risky since possible side effects of the drug may be more easily avoided or compensated for by prematurely interrupting the infusion. In this embodiment, the system can repeat the sequence of inflating the balloons, perfusing the drug and deflating the balloons several times. The sequence preferably is programmed in terms of both the quantity of the drug for each infusion, and the time interval between consecutive operations.

Figure 2:
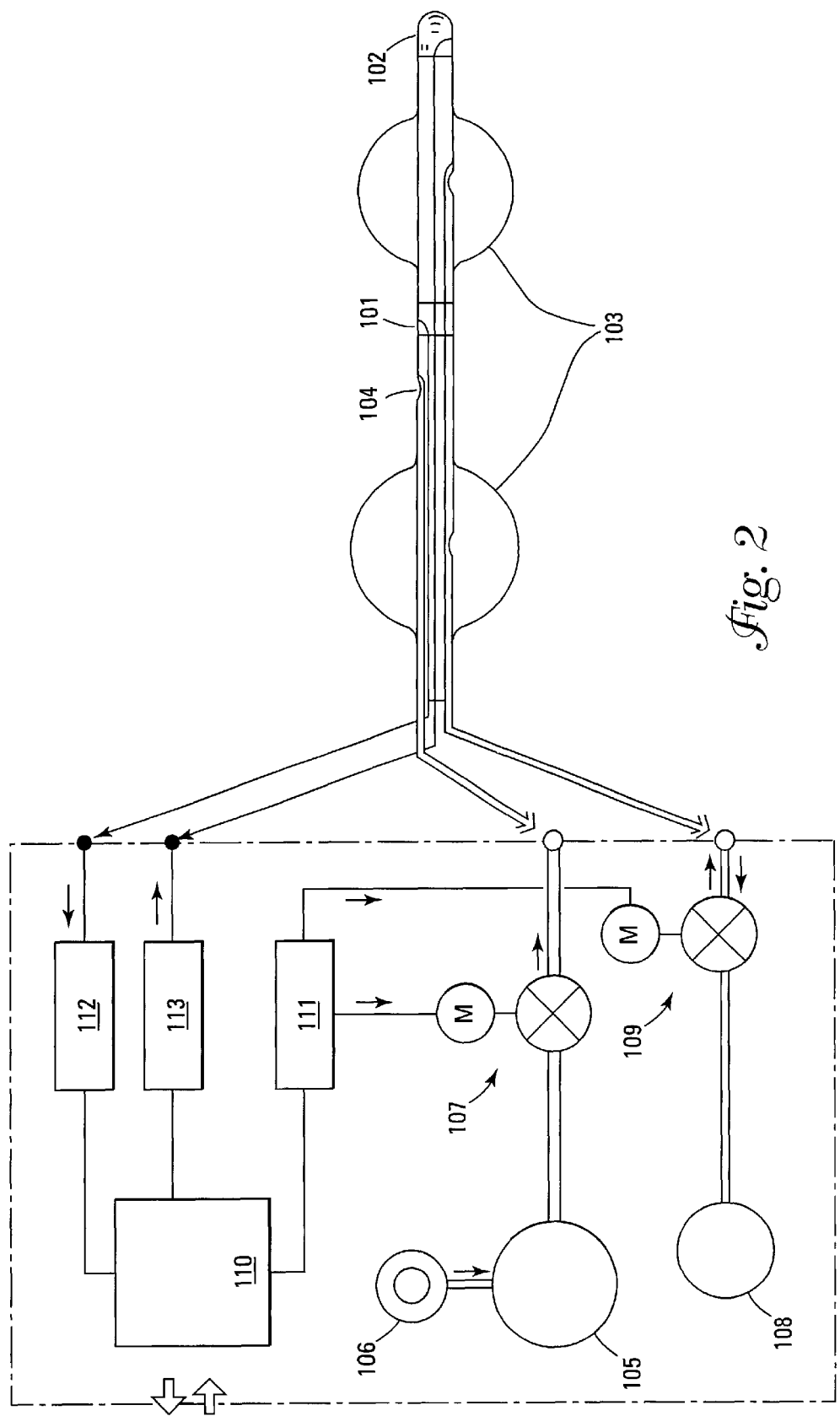
FIG. 2 is a schematic depiction of an implantable device for detecting and interrupting atrial fibrillation.

FIG. 2 schematically depicts an implantable device which is preferably implanted into the coronary sinus. In the Figure, only the distal section of the electrocatheter is shown.

The system can include a catheter fitted with two balloons 103, which are controlled simultaneously by a fluid which is pumped through an inflation lumen in communication with the interior of each balloon.

One or more sensors 101 for detecting atrial electrical activity and AF can be included. In addition, an electrode 102 can be provided for emergency stimulation.

The balloons can be positioned on the catheter such that when the balloons are inflated, the distal balloon occludes the vena magna where it rises in the CS, and the proximal balloon occludes the entry of the CS into the right atrium. Upon inflation of the balloons, a chamber is formed between them, with the oblique vein of Marshall opening into this chamber. An appropriate drug can be injected into the chamber at a pressure which forces it into the aforesaid vein. Further detail is provided below. (See FIG. 5 and its description).

The circuitry which operates the device is contained in a sealed, biocompatible housing, which is connectable to the electrocatheter. The housing contains a battery, (not shown in the drawing); a drug reservoir 105 which can be filled from outside the body through a permeable gate 106; an electrically controlled pump 107 for the infusion, whose operative characteristics and operation time are programmed depending on the desired dose of the drug to be administered to the patient; an inflation reservoir 108 containing a biocompatible liquid or inert gas for inflating the balloons 103; a reversible pump 109 for inflating and deflating the balloons; a circuit 111 for controlling the balloon inflation and deflation system; a circuit 112 connected to the sensor 101 for detecting atrial activity and AF; a circuit 113 for emergency stimulation; and a circuit 110 for programming the system with characteristics imposed telemetrically from outside the body.

Figure 3:
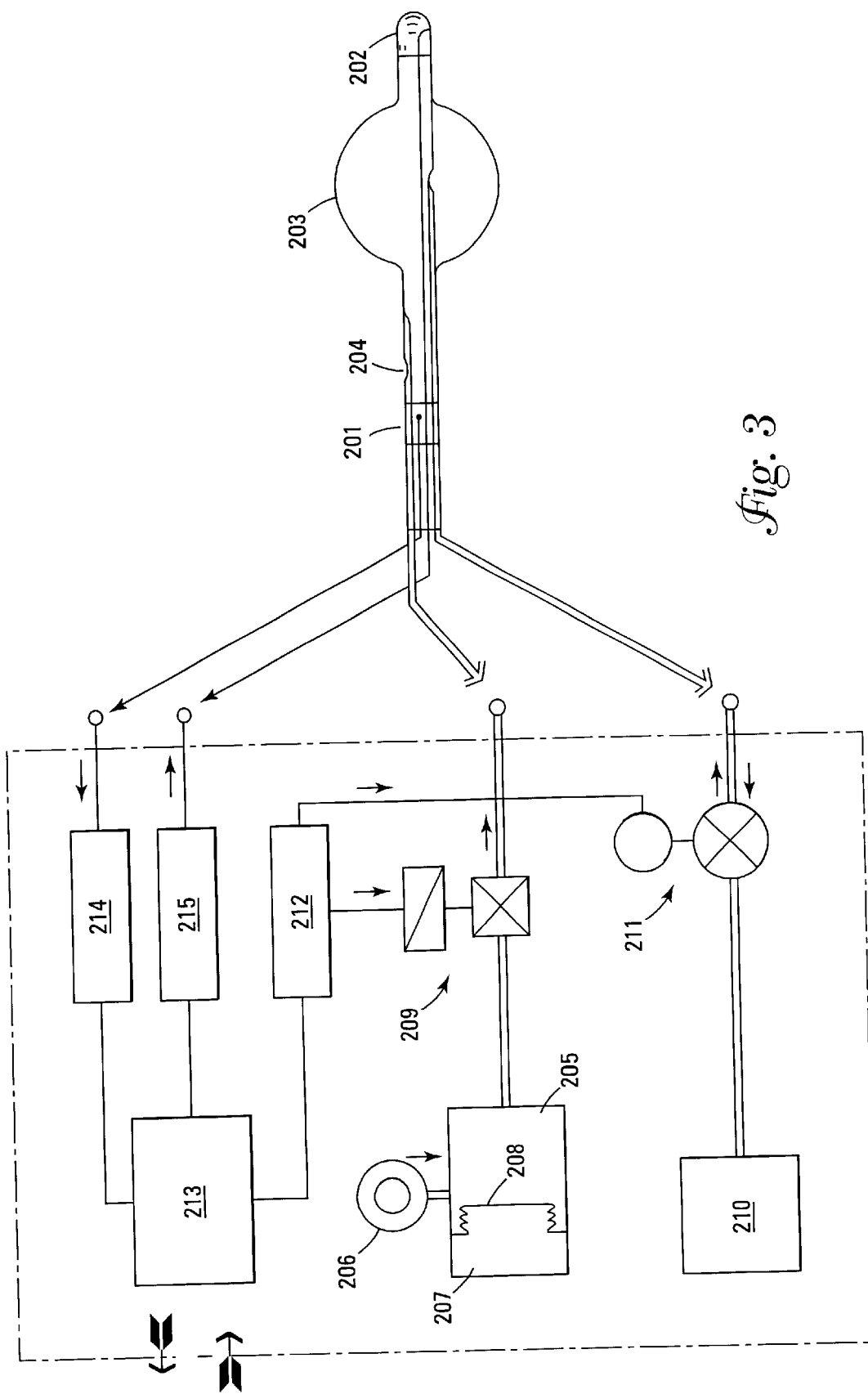
FIG. 3 is an alternative embodiment of the device of FIG. 2.

A second embodiment of the invention is schematically shown in FIG. 3. The device of the second embodiment is also intended for CS infusion. In FIG. 3, only the distal part of the electrocatheter is shown. The device of FIG. 3 includes one or more sensors 201 for detecting atrial activity and AF; an electrode 202 for optimally providing stimulation; a balloon 203 disposed distally downstream of the vein of Marshall for closing the input of the vena magna; and a drug infusion lumen 204.

The device also includes a battery (not shown) for providing power to the electrical and electronic components; a drug reservoir 205 which can be filled from the outside through a port 206; a gas reservoir 207 containing an inert gas (i.e., helium or similar) under pressure and separated from the liquid drug by a resilient membrane wall 208; a solenoid 209 controlled by the electronic system, which opens for the time necessary for administration of the drug; an inflation reservoir 210 containing an inert liquid or gas for inflating the balloon or balloons; an electrically driven pump 211 which alternatively inflates and deflates the balloon when the program requires it; a circuit 212 for controlling the hydraulic system driven by the program inserted in the circuit 213; a programming circuit 213 whose characteristics are imposed telemetrically from the outside; a circuit 214 for sensing atrial activity and AF; and a circuit 215 for emergency stimulation.

The construction of the electrocatheter, as shown in FIGS. 2 and 3, depends on the arrangement chosen for the infusion of the drug into the CS. FIGS. 4A–4D schematically depict several possible embodiments of the electrocatheter. In FIGS. 4A–4D, the CS is indicated 32, and the oblique vein of Marshall which rises from the left atrium is indicated 31. The drawings show various embodiments for obtaining the infusion of the drug in the atrial wall.

Figure 4A:
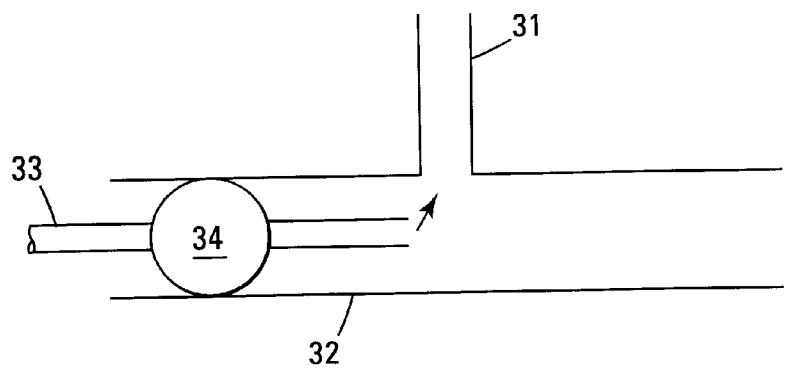
FIGS. 4A–4D are schematic representations of several embodiments of the method of use of a catheter employed by the inventive device.
Figure 4B:
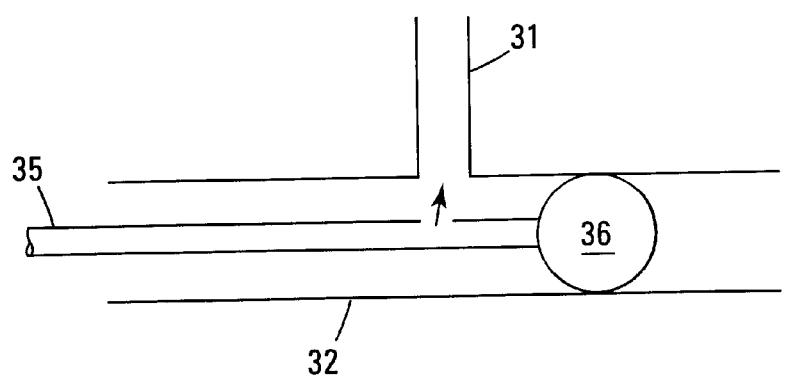
Figure 4C:
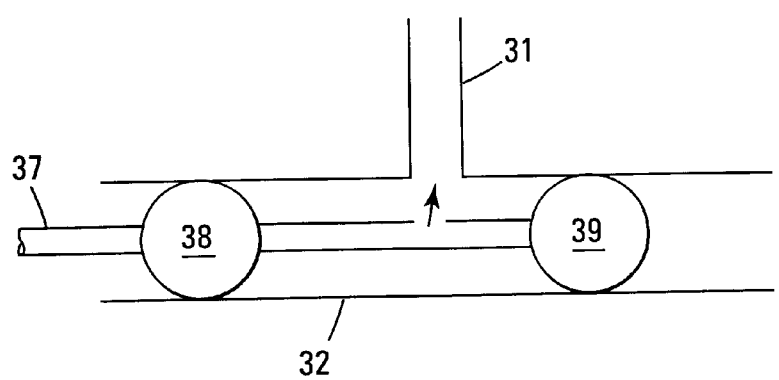

In the embodiments of FIG. 4A, FIG. 4B and FIG. 4C, the arrangement of the hydraulic ducts does not vary with respect to that shown in FIGS. 2 and 3, apart from the fact that the lumen which carries the fluid for inflating the balloons has to communicate with each balloon, and the lumen for the infusion of the drug must be open in the predetermined zone. On the other hand, the embodiment of FIG. 4D includes a catheter dedicated to infusion which is orientable for the cannulation of the vein of Marshall or just the CS.

In FIG. 4A the balloon 34 occludes the entry of the CS in the right atrium. By injecting the drug and applying the venous pressure arising from the coronary veins (vena magna), the drug will be forced into the vein 31, but also partly into the ventricles.

In FIG. 4B the balloon 36 closes the CS downstream of the vein 31 (with respect to normal blood flow). Perfusion through the catheter 35 at the correct pressure encourages the entry of the drug into the vein 31, although with some loss to the right atrium.

In FIG. 4C, two balloons are in communication with the same lumen which inflates them at the same time. These balloons, 38 and 39, thus define the ends of a chamber which facilitates the infusion of the drug in the vein 31.

Figure 4D:
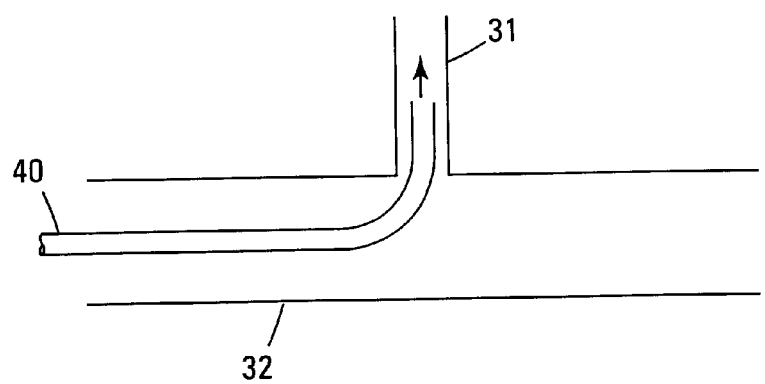

In FIG. 4D a catheter 40 is provided which is sufficiently flexible and thin so as to be able to cannulate the vein 31 or just the CS. In this case it may be necessary to use different catheters to support the sensor and the stimulation electrode.

For long-term implantation, the catheter must be constructed in such a way so as to avoid the formation of clots on its structure, especially at the outlet positioned near the distal end of the catheter through which the drug exits the device. To avoid blood passing through into the drug delivery lumen, (which could result in coagulation and occlusion), a valve may be used. The valve may be formed as shown schematically in FIG. 5. On a section of the catheter which includes the outlet hole 300, appropriately shaped for uniformity of diameter, is a segment of tubing 302 formed of a resilient biocompatible material, with a very thin wall and a hole 304 at one end. The position of this sleeve is such that the outlet hole 300 is covered and the hole 304 does not coincide with the outlet hole 300 on the catheter. The sleeve is fitted to the end 306 opposite the hole 304 which must remain open.

When the pump delivers the drug through the drug delivery lumen 308, the pressure exerted is set such that it can lift the free edge of the resilient sleeve, permitting the liquid to exit from the hole 304 and/or the free end 310 of the sleeve itself.

As an alternative embodiment, a "porous" catheter segment can be inserted in the section of the catheter from which the drug is to be released. The structure of the catheter material may be made permeable using various techniques to create a porosity with holes compatible in size with the molecular structure of the drug to be infused (for example, with diameters of approximately 20 $\mu$m). The drug is forced out of the catheter by means of a suitable pressure.

The advantages in using a system of the type described above lie in the timeliness of the therapeutic intervention which protects the patient from pooling of blood in the atrium, thus removing the risk of the formation and propagation of thromboses, and in the possibility of pharmacological intervention at the onset of AF, when the intervention threshold is lower. This enables the use of smaller quantities of the drug in comparison with later intervention, as currently occurs with the pharmacological or electrical treatments currently practiced.

Where a catheter for the atrial injection of the drug is employed, the preferred configurations are those of FIGS. 2 and 3 in which, however, the operation of the block 110 or 213, and the adjacent blocks must be implemented, and in which the catheter no longer carries the balloons. The mechanical simplification of the catheter is balanced by the greater complexity of the necessary program for the CPU which must be contained in 110 or 213. It should be noted, however, that in this embodiment the introduction of the drug into the atrium requires a greater quantity of drug, approximately 5–6 times that necessary in the CS. This increases the likelihood of collateral effects of the drug, which makes the strict monitoring of the electrical (and mechanical) characteristics of the heart necessary. However, such monitoring is also useful and advisable even for embodiments in which the drug is to be introduced into the CS solution.

The electrical characteristics to be monitored are a) cardiac rate; b) QRS duration; c) the distance PQ; d) QTc length; e) the onset of A-V block; and f) cardiac muscle contractility.

In the embodiments of the inventive system, all or just some of the aforesaid parameters may be monitored. These parameters may be detected by means of electrodes and sensors positioned on the catheter so as to detect the atrial electrical activity, ventricular electrical activity, and muscular activity.

If the electrocatheter (including the drug-infusion lumen) with an electrode at the distal end is positioned in the right ventricle (RV), and with proximal electrodes in the right atrium (RA), the logistic situation is similar to that of the "single lead" electrocatheters for VDD stimulation. In this case, the lumen for the drug opens into the RA for atrial infusion, or it could open into the RV for entry of the drug into circulation. The contractility sensor is disposed distally in the ventricle. One preferred sensor is the BEST sensor commercially available from SORIN BIOMEDICA S.p.A., Saluggia, Italy.

Alternatively, if the electrocatheter is inserted in the CS with the associated balloons, atrial activity may be detected by electrodes situated in the CS, while ventricular activity may be detected by extending the catheter to the vena magna, with a distally disposed electrode, together with the contractility sensor.

With these possible arrangements, all of the electrical signals necessary to obtain the parameters discussed above are available. Once received, they may be sent to the CPU for processing so as evaluate the necessary parameters.

The program for telemetrically connecting with or sending to the CPU must provide for a break in supply if the parameters vary outside the programmed thresholds. These include a) an increase or decrease in cardiac rate from the predetermined thresholds and/or possible arrhythmia, (in this case, the infusion of the drug is stopped and emergency stimulation may be activated); b) an increase in QRS duration, (infusion is stopped); c) an increase in PQ, (infusion is stopped); d) an increase in QTc, (infusion is stopped); e) onset of AV block, (infusion is stopped); and f) a reduction in contractility, (infusion is stopped).

An instrument such as that described may advantageously be provided with a system which uses a microcontroller (or a microprocessor) in order to obtain maximum functional flexibility.

Figure 6:
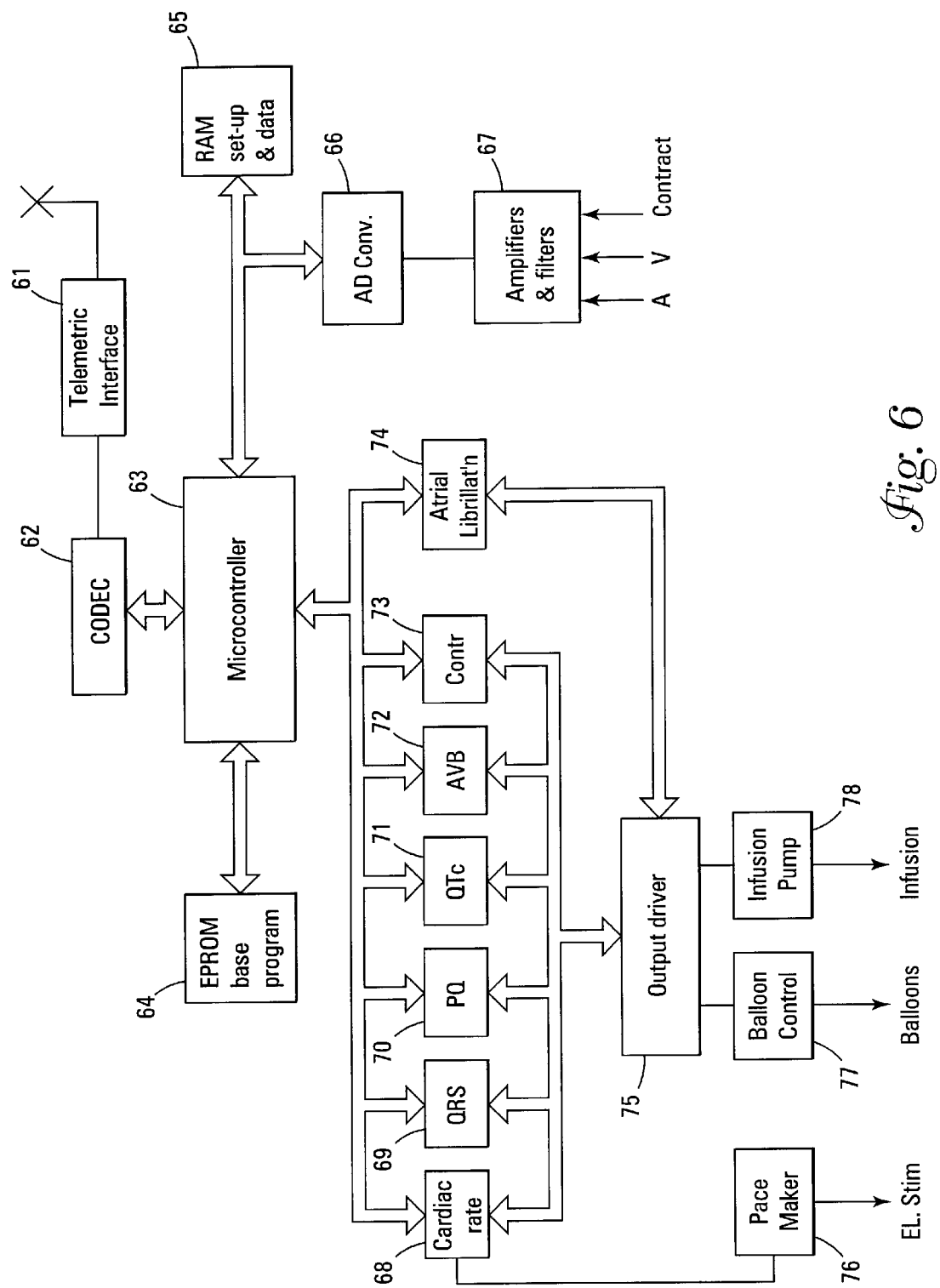
FIG. 6 is a schematic block diagram depicting the various control circuits of the present invention.

FIG. 6 is a schematic depiction of one embodiment of the control structure for the inventive system. A telemetric interface 61 enables the acquisition of data or the sending of commands by means of a coupling (electric, electromagnetic, RF) to and from the outside, via a coder/decoder (CODEC) 62 which joins with a transmitter-receiver outside the body. A base program contained in EPROM memory 64 uses the commands received by the telemetric means to control, by means of a microcontroller 63, the drug infusion and emergency stimulation programs. These programs are controlled by interfaces 68–74 in accordance with the parameters of the signals detected through the electrocatheter. The signals are processed by amplifiers and filters contained in block 67, and converted from analog to digital form by AD converter block 66.

An interface 74, in the presence of ECG signals with AF, activates an output driver 75 for the drug infusion cycle. In this circumstance, block 77 provides for the inflation and deflation of the optional balloons (when they are present) and block 78 specifies the drug infusion cycle.

The interfaces 68–73 contain the intervention thresholds. These interfaces will interrupt the infusion cycle when the relevant thresholds are exceeded.

If interface 68, (which relates to cardiac rate), detects cardiac arrest or bradycardia at a level below the threshold, it will enable emergency stimulation by means of block 76, in accordance with the characteristics inserted in program 64.

All of the data relating to the parameters received telemetrically and which constitute the SET UP of the infusion-stimulation system are stored in a RAM 65 which also stores the data acquired from the AD converter 66 and which is processed by the microcontroller 63 for the various interfaces 68–74. It is thus possible to retransmit to the outside, coded by CODEC 62, both the state of the parameters of operation and the received and processed data. It is noted that there are currently available integrated systems which contain the majority of the blocks indicated in the drawings, as well as the microcontroller, in a single chip, with advantages of storage and energy supply.

Figure 5:
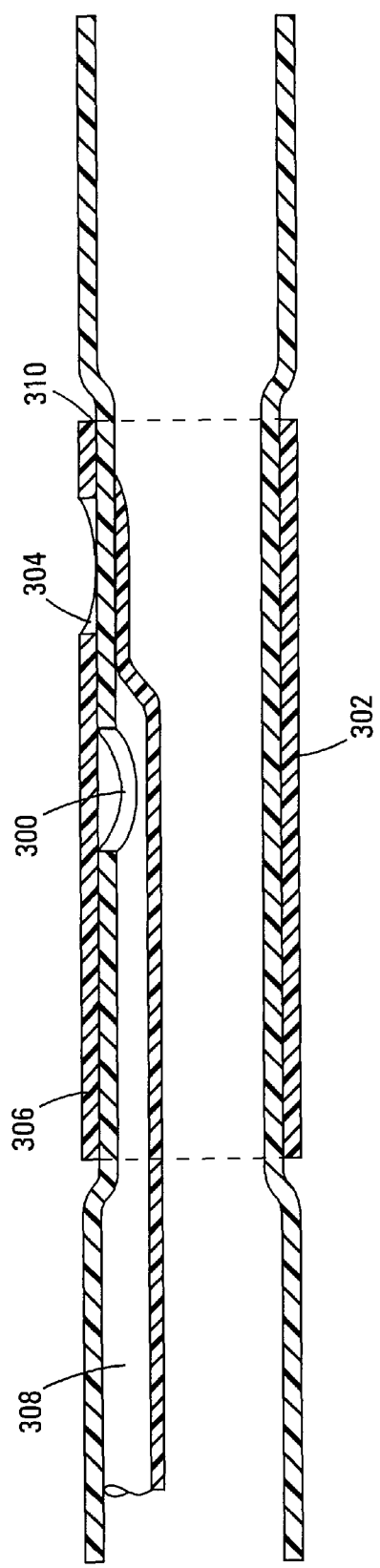
FIG. 5 is a schematic representation of one embodiment of a drug outlet valve for use in connection with the catheter of the present invention.
Figure 7:
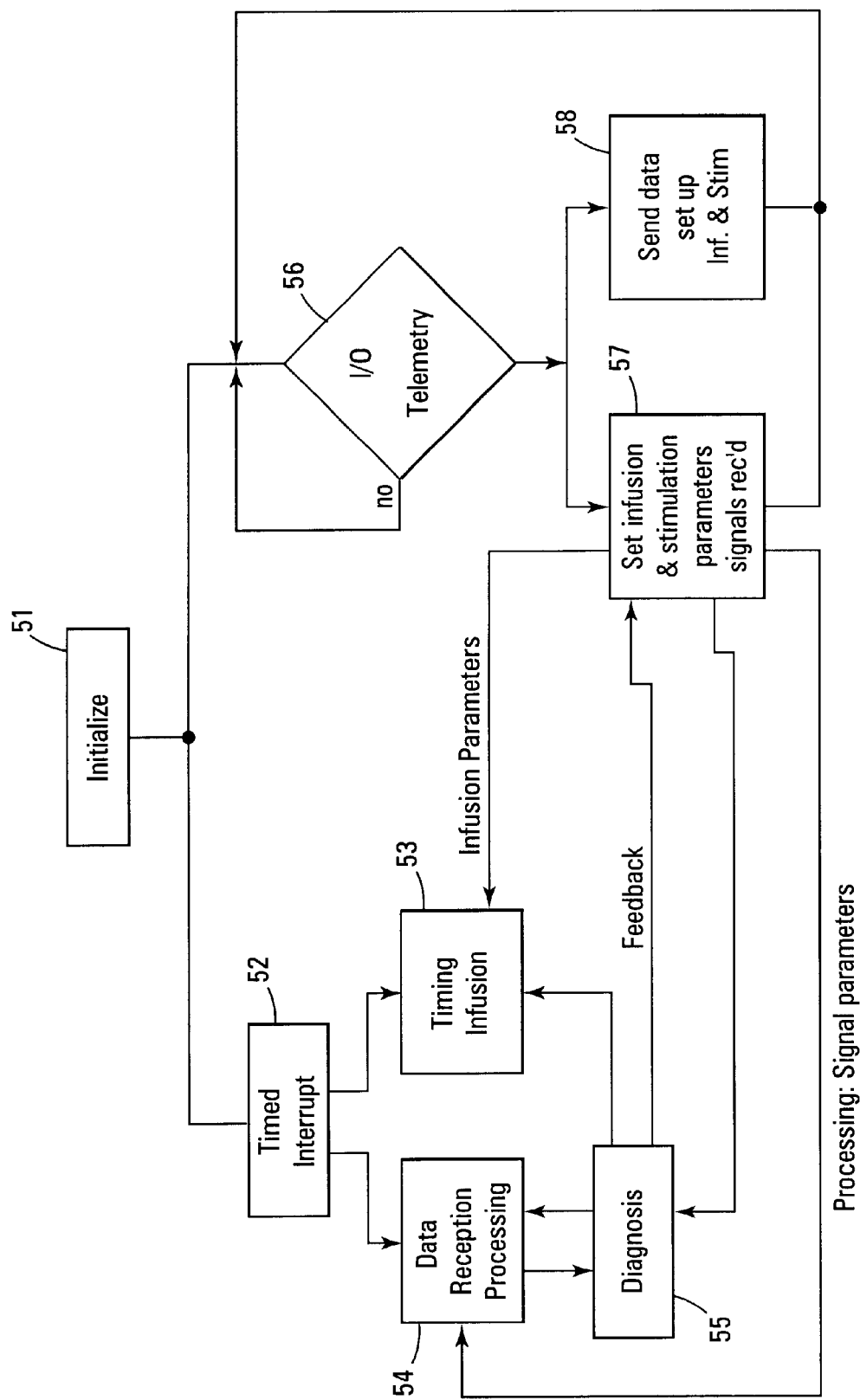
FIG. 7 is a flow chart depicting one embodiment of software for use with the inventive device.

A possible flow chart of the software for the system of FIG. 5 is shown in FIG. 7. The initialization block 51 is employed at the beginning of the system. It activates all the peripherals (timer, data transmission and reception etc.), and imposes the default parameters for drug infusion, for processing the required cardiac parameters, and for possible feedback between the received signals and infusion. This data can then be modified telemetrically by the user.

The real-time processes to be employed are represented by blocks 53 and 54. A timed interrupt 52 activates the processes of these blocks with absolute priority. The timer must be set correctly for the frequency at which the systems for the A/D conversion of the block 54 must operate, being those for the infusion and the generation of emergency stimulation pulses by the block 53. The timer generates an interrupt for the CPU in such a way as to give precedence to these processes.

The block 54 is able to accumulate, in memory, the data necessary for the processing of the parameters and subsequently sends them to block 55 which contains the appropriate diagnostic algorithms and consequent feedback on the infusion and emergency stimulation parameters. These functions may be performed or modified by the external user.

In the interval between interrupts, the CPU tests the telemetric I/O interface 56 to establish whether there is a requirement for data (which will be provided by block 58) or a command code for the imposition or modification of the infusion or stimulation parameters by block 57. If data (cardiac parameters, ECG, status of infusion or stimulation data) is required, block 58 is enabled to send the data to the coding and telemetry system. In the case of imposition or modification of the intervention parameters, block 57 will, from time to time, set infusion or stimulation data, or data for acquisition of external signals (parameter type, signal type etc.).

When the interaction between the signals received and the decision to intervene is enabled, the diagnostic block 55 is able to act with the required algorithm, activating feedback with the block 57.

In addition to being used for cardioversion of atrial arrhythmias, the system may be used for the administration of cardioactive drugs which act specifically on the myocardium or on its conduction apparatus. In these cases, it is important that the administration program, in the case of an implantable system such as that described, is easily adaptable to the needs of the patient by telemetric means, while also retaining the monitoring of the electromechanical characteristics of the heart, which react to the infusion.

EQUIVALENTS

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A medical device adapted for implantation in a patient's body for treatment of atrial arrythmia, comprising:
    a catheter having a distal end and a proximal end, the catheter having at least one expandable balloon positioned near its distal end, a drug delivery outlet and first and second lumens, the first lumen being connected to the drug delivery outlet, and the second lumen being connected to the expandable balloon, the catheter further having at least one sensing electrode and at least one stimulation electrode, each sensing and stimulation electrode being connected to a separate conductor;
    a housing connected to the proximal end of the catheter;
    first and second pumps contained within the housing;
    first and second reservoirs contained within the housing, the first reservoir being connected to the first lumen and configured to contain a drug, the second reservoir being connected to the second lumen and configured to contain an inflation medium including one of a liquid and a gas, the first pump being connected such that the drug is pumped from the first reservoir through the first lumen and out the drug delivery outlet when the first pump is activated, the second pump being connected such that the inflation medium is pumped from the second reservoir through the second lumen into the balloon when the second pump is activated;
    a first circuit connected to the at least one sensing electrode through a respective conductor, the first circuit being configured for sensing electrical activity of the patient's heart including atrial fibrillation and at least one of cardiac rate, QRS duration, PQ distance, QTc length, onset of A-V block, and cardiac muscle contractility, the first circuit configured to generate at least one output signal indicative of the sensed electrical activity; and a second circuit connected to receive the at least one output signal from the first circuit and configured to generate a first activation signal when atrial fibrillation is sensed, the second circuit being connected to provide the first activation signal to the first pump to activate the first pump, such that the drug is delivered through the drug delivery outlet when the first activation signal is provided to the first pump, the second circuit being configured to terminate the first activation signal upon sensing at least one of an increase in cardiac rate above a predetermined high rate threshold, a decrease in cardiac rate below a predetermined low rate threshold, an increase in QRS duration above a predetermined QRS threshold, an increase in PQ distance above a predetermined threshold PQ distance, an increase in QTc length above a predetermined threshold QTc length, the onset of A-V block and a reduction in cardiac muscle contractility below a predetermined threshold cardiac muscle contractility.

2. The medical device of claim 1 further comprising a two-way telemetry circuit connected so that the first circuit and the second circuit are externally programmable.

3. The medical device of claim 2 wherein the telemetry circuit further comprises a microcontroller.

4. The medical device of claim 3 wherein the microcontroller is capable of stopping drug infusion upon detection of predetermined thresholds.

5. The medical device of claim 1 wherein the second circuit is configured to generate a second activation signal when atrial fibrillation is sensed, the second circuit being connected to provide the second activation signal to the second pump such that the inflation medium is pumped into the at least one balloon when the second activation signal is provided to the second pump.

6. The medical device of claim 1 wherein the first activation signal comprises a first programmed infusion cycle having programmable parameters including at least one of drug dosage and time of drug administration.

7. The medical device of claim 1 wherein the first reservoir further comprises a port for filling the first reservoir.

8. The medical device of claim 1 wherein the first pump is a mechanical pump.

9. The medical device of claim 1 wherein the drug delivery outlet comprises a one-way valve.

10. The medical device of claim 1 wherein the drug delivery outlet comprises a porous segment through which the drug may be released.

* * * * *